(12) United States Patent
Kishimoto et al.

(10) Patent No.: US 8,183,413 B2
(45) Date of Patent: May 22, 2012

(54) PROCESS FOR PRODUCTION OF β-AMINO-α-HYDROXY CARBOXAMIDE DERIVATIVE

(75) Inventors: Narumi Kishimoto, Takasago (JP); Hiroaki Yasukouchi, Takasago (JP); Toshihiro Takeda, Takasago (JP)

(73) Assignee: Kaneka Corporation, Osaka (JP)

( * ) Notice: Subject to any disclaimer, the term of this patent is extended or adjusted under 35 U.S.C. 154(b) by 889 days.

(21) Appl. No.: 12/223,036

(22) PCT Filed: Jan. 16, 2007

(86) PCT No.: PCT/JP2007/050485
§ 371 (c)(1),
(2), (4) Date: Jul. 21, 2008

(87) PCT Pub. No.: WO2007/083620
PCT Pub. Date: Jul. 26, 2007

(65) Prior Publication Data
US 2009/0312577 A1   Dec. 17, 2009

(30) Foreign Application Priority Data

Apr. 20, 2006  (JP) ................................. 2006-012904

(51) Int. Cl.
C07C 231/02  (2006.01)
(52) U.S. Cl. .................. 564/138; 564/139; 564/141
(58) Field of Classification Search .................. 564/296
See application file for complete search history.

(56) References Cited

U.S. PATENT DOCUMENTS

| | | |
|---|---|---|
| 6,020,518 A | 2/2000 | Matsumoto et al. |
| 6,376,649 B1 | 4/2002 | Semple et al. |
| 6,573,399 B1 | 6/2003 | Nishiyama et al. |
| 2003/0171597 A1 | 9/2003 | Katoh et al. |
| 2005/0153900 A1 | 7/2005 | Velazquez et al. |
| 2005/0197299 A1 | 9/2005 | Babine et al. |
| 2005/0197301 A1 | 9/2005 | Njoroge et al. |

FOREIGN PATENT DOCUMENTS

| | | |
|---|---|---|
| EP | 0 490 667 | 6/1992 |
| JP | 61-129159 | 6/1986 |
| JP | 5-170722 | 7/1993 |
| JP | 2001-328971 | 11/2001 |
| JP | 2002-532466 | 10/2002 |
| JP | 2004-517047 | 6/2004 |
| WO | 98/07687 | 2/1998 |
| WO | 00/53575 | 9/2000 |
| WO | 02/18369 | 3/2002 |
| WO | 02/18639 | 3/2002 |
| WO | 2005/058821 | 6/2005 |

OTHER PUBLICATIONS

Extended European Search issued Jul. 22, 2011 in corresponding European application No. 07706812.
W. Pearson et al., Synthesis of β-Amino-α-hydroxy Acids via Aldol Condensation of a Chiral Glycolate Enolate, Synthesis of (−)-Bestatin, J. Org. Chem., vol. 54, pp. 4235-4237, 1989.
W. Lubisch et al., Benzoylalanine-Derived Ketoamides Carrying Vinylbenzyl Amino Residues: Discovery of Potent Water-Soluble Calpain Inhibitors with Oral Bioavailability, J. Med Chem., vol. 46, pp. 2404-2412, 2003.
International Search Report issued Mar. 13, 2007 in the International (PCT) Application PCT/JP2007/050485 of which the present application is the U.S. National Stage.
Translation of PCT Written Opinion issued Mar. 13, 2007 in connection with PCT/JP 2007/050485 corresponding to the present US application.

*Primary Examiner* — Brian J Davis
(74) *Attorney, Agent, or Firm* — Wenderoth, Lind & Ponack, L.L.P.

(57) ABSTRACT

Provided is a process for production of a β-amino-α-hydroxy carboxamide derivative that is important in production of drugs or the like. In the presence of a predetermined solvent, a β-(N-protected)amino-α-hydroxycarboxylic acid is reacted with an amine to conversion to a β-(N-protected)amino-α-hydroxy carboxamide derivative; then the derivative is deprotected for conversion to a β-amino-α-hydroxy carboxamide derivative; and the derivative is crystallized using a protic solvent to obtain a crystal. The high-purity β-amino-α-hydroxy carboxamide derivative can be stably produced on an industrial scale by the process.

12 Claims, No Drawings

PROCESS FOR PRODUCTION OF β-AMINO-α-HYDROXY CARBOXAMIDE DERIVATIVE

TECHNICAL FIELD

The present invention relates to a process for production of a β-amino-α-hydroxy carboxamide (β-amino-α-hydroxy acid amide) derivative that is useful as a production intermediate for various protease inhibitors. The derivative is represented by the general formula (1);

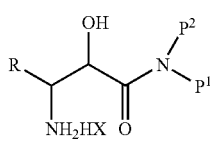

(1)

(wherein R represents an alkyl group having 1 to 6 carbon atoms and optionally having a substituent, or an aralkyl group having 7 to 15 carbon atoms and optionally having a substituent; $P^1$ and $P^2$ each independently represent a hydrogen atom, an alkyl group having 1 to 6 carbon atoms and optionally having a substituent, an aralkyl group having 7 to 15 carbon atoms and optionally having a substituent, or a carboxyl group; HX represents a mineral acid, a sulfonic acid or a carboxylic acid).

BACKGROUND ART

The β-amino-α-hydroxy carboxamide derivative (1) obtained according to the production process of the present invention is important intermediates for the production of drugs such as antiviral agents (see Patent Document 1). These compounds are used as, for example, intermediates for HIV protease inhibitors and hepatitis C remedies.

Conventionally, as a process for producing the β-amino-α-hydroxy carboxamide derivative (1), for example, there have been reported;

(i) a process for production of (3S)-3-amino-2-hydroxy-4-phenylbutanoic acid cyclohexylmethylamide hydrochloride by dissolving (3S)-3-N-(tert-butoxycarbonyl)amino-2-hydroxy-4-phenylbutanoic acid in DMF, reacting the solution with cyclohexylmethylamine, N-hydroxy-norbornene-2,3-dicarboxylimide (HOBN) and 1-ethyl-3-(3-N,N-dimethylaminopropyl)carbodiimide (EDC) hydrochloride added thereto for conversion to (3S)-3-N-(tert-butoxycarbonyl)amino-2-hydroxy-4-phenylbutanoic acid cyclohexylmethylamide, and thereafter adding 4 N-hydrochloric acid/dioxane thereto for removal of Boc, then purifying the deprotected compound by column chromatography (chloroform/methanol) in the presence of ether, and again adding 4 N-hydrochloric acid/dioxane thereto (see Patent Document 2);

(ii) a process for production of (3S)-3-amino-2-hydroxyhexanoic acid cyclopropylamide by reacting (2S)-2-N-carbamate-protected amino-2-alkyl-ethanal with cyclopropylisonitrile for conversion to (3S)-3-N-carbamate-protected amino-2-acyloxypropanoic acid cyclopropylamide, then deprotecting the 2-positioned hydroxyl group, and further removing Boc using 4 N-hydrochloric acid/dioxane, and thereafter evaporating away the solvent (see Patent Document 3).

However, the conventional methods have some problems for industrial scale production in that unfavorable reagents, such as DMF, chloroform and 1,4-dioxane having a problem of negative influence on the environment, diethyl ether that is an extremely highly flammable organic solvent, isonitrile derivatives having disadvantage in point of bad smell and production difficulty, are used, and large quantities of plural organic solvents are used.

In the conventional process for purification of the β-amino-α-hydroxy carboxamide derivative (1), disclosed is a process of column chromatography (eluent: chloroform/methanol) as a purification method. The process has serious problems for industrial scale production in that a large quantity of an unfavorable solvent such as chloroform is used, steps are complicated, the number and the volume of the production apparatuses are increased, and the yield is low. Further, in the conventional process, for example, disclosed is a process for obtaining (3S)-3-amino-2-hydroxyhexanoic acid cyclopropylamide hydrochloride as a crystal by evaporating the solvent from a mixture with 1,4-dioxane. However, it has been found by investigations of the present inventors that 3-amino-2-hydroxyhexanoic acid cyclopropylamide hydrochloride is solidified during the solvent evaporation in the process, and as a result, stirring becomes impossible. It has been found that the crystal is extremely difficult to be filtered. The both of the above condition result is that the operation could no more be continued or the operation time is prolonged, and therefore, it could not be said that the process may be suitable for industrial scale.

As mentioned above, the β-amino-α-hydroxy amide derivative (1) is intermediate for HIV protease inhibitors and hepatitis C remedies to be taken in a large dose, and therefore development of a practicable process for the mass-production thereof has a particularly important meaning.

Patent Document 1: WO02/018639
Patent Document 2: JP-A 5-170722
Patent Document 3: WO05/058821

DISCLOSURE OF THE INVENTION

Problems to be Solved by the Invention

In consideration of the above-mentioned current situation, an object of the present invention is to provide an industrially advantageous process for production of the β-amino-α-hydroxy carboxamide derivative (1).

Means for Solving the Problems

The present inventors have earnestly studied for the purpose of solving the above-mentioned problems. As a result, the inventors have found that, regarding amidation reaction of a β-(N-protected)amino-α-hydroxycarboxylic acid with an amine using a condensing agent, the amidation can be efficiently attained in a solvent such as ethyl acetate or other esters and tetrahydrofuran or other ethers. In particular, the inventors have found that the amidation can be efficiently attained in the presence of water. Further, it has been found that, in a step of crystallization of the β-amino-α-hydroxy carboxamide derivative (1) in the presence of a protic solvent, the crystallization slurry of the derivative can have good flowability and can give a crystal of good filterability, and the β-amino-α-hydroxy carboxamide derivative (1) of high purity can be obtained. In addition, the inventors have found that the β-(N-protected)amino-α-hydroxy carboxamide derivative may be obtained as a crystal having the property of good flowability can be obtained under a specific crystallization condition.

The present invention relate to a process for production of a β-amino-α-hydroxy carboxamide derivative (1) of the following general formula (1);

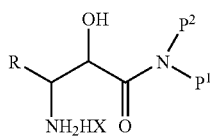
(1)

(wherein R represents an alkyl group having 1 to 6 carbon atoms and optionally having a substituent, or an aralkyl group having 7 to 15 carbon atoms and optionally having a substituent; $P^1$ and $P^2$ each independently represent a hydrogen atom, an alkyl group having 1 to 6 carbon atoms and optionally having a substituent, an aralkyl group having 7 to 15 carbon atoms and optionally having a substituent, or a carboxyl group; HX represents a mineral acid, a sulfonic acid, or a carboxylic acid)
characterized in that the β-amino-α-hydroxy carboxamide derivative (1) is obtained as a crystal by a crystallization step using a solvent containing a protic solvent.

The invention also relates to a process for production of a β-(N-protected)amino-α-hydroxy carboxamide derivative of the following general formula (4);

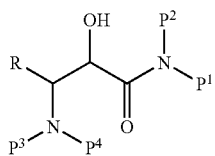
(4)

(wherein R represents an alkyl group having 1 to 6 carbon atoms and optionally having a substituent, or an aralkyl group having 7 to 15 carbon atoms and optionally having a substituent; $P^1$ and $P^2$ each independently represent a hydrogen atom, an alkyl group having 1 to 6 carbon atoms and optionally having a substituent, an aralkyl group having 7 to 15 carbon atoms and optionally having a substituent, or a carboxyl group; $P^3$ and $P^4$ each independently represent a hydrogen atom or a protective group for the amino group, or are joined together to form a phthaloyl group)
characterized in that a β-(N-protected)amino-α-hydroxy carboxamide derivative containing at least an optical isomer thereof as an impurity is crystallized;
wherein at least one step of the following steps i) to iii):
i) a step of crystal dissolution
ii) a cooling step
iii) a step of seed crystal addition
is included.

The invention also relates to a process for production of a β-(N-protected)amino-α-hydroxy carboxamide derivative of the following general formula (4);

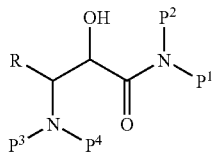
(4)

(wherein R represents an alkyl group having 1 to 6 carbon atoms and optionally having a substituent, or an aralkyl group having 7 to 15 carbon atoms and optionally having a substituent; $P^1$ and $P^2$ each independently represent a hydrogen atom, an alkyl group having 1 to 6 carbon atoms and optionally having a substituent, an aralkyl group having 7 to 15 carbon atoms and optionally having a substituent, or a carboxyl group; $P^3$ and $P^4$ each independently represent a hydrogen atom or a protective group for the amino group, or are joined together to form a phthaloyl group),
characterized in that a β-amino-α-hydroxycarboxylic acid of the following general formula (2);

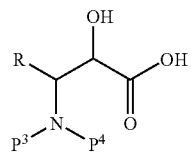
(2)

(wherein R, $P^3$ and $P^4$ are the same as above)
is reacted with a condensing agent and an amine of the general formula (3);

(3)

(wherein $P^1$ and $P^2$ are the same as above)
in the presence of one or more solvents of aliphatic esters, ethers, nitrites and sulfur-containing solvents.

Effect of the Invention

According to the present invention, the β-amino-α-hydroxy carboxamide derivative (1) can be simply and efficiently produced with extremely high productivity.

BEST MODE FOR CARRYING OUT THE INVENTION

Hereinafter, the present invention is described in detail.

Production of the β-(N-protected)amino-α-hydroxy carboxamide derivative (4)

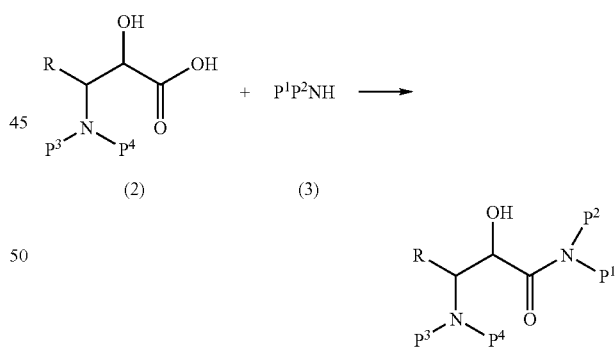

The β-(N-protected)amino-α-hydroxy carboxamide derivative (4) can be obtained by condensation reaction of a β-(N-protected)amino-α-hydroxycarboxylic acid (2) and an amine (3).

In the above general formulae (2) and (4), R represents an alkyl group having 1 to 6 carbon atoms and optionally having a substituent, or an aralkyl group having 7 to 15 carbon atoms and optionally having a substituent. The alkyl group having 1 to 6 carbon atoms is not specifically limited, but includes, for example, a methyl group, an ethyl group, an n-propyl group, an isopropyl group, an n-butyl group, a sec-butyl group, a tert-butyl group, a pentyl group, and a hexyl group; preferably an n-propyl group, an isopropyl group, and an n-butyl group; more preferably an n-propyl group. The substituent is not specifically limited, but includes, for example, a halogen atom, an amino group, and a hydroxyl group; and preferably a halogen atom.

The aralkyl group having 7 to 15 carbon atoms and optionally having a substituent includes, for example, a benzyl group, a p-chlorobenzyl group, a p-hydroxybenzyl group, a p-fluorobenzyl group, an m,m-difluorobenzyl group, a phenylethyl group, and a naphthyl group. The group is preferably an aralkyl group having 7 or 8 carbon atoms, more preferably a benzyl group. The substituent is not specifically limited, but includes, for example, a halogen atom, an amino group, and a hydroxyl group, and preferably a halogen atom.

$P^1$ and $P^2$ in the above general formulae (3) and (4) each independently represent a hydrogen atom, an alkyl group having 1 to 6 carbon atoms and optionally having a substituent, an aralkyl group having 7 to 15 carbon atoms and optionally having a substituent, or a carboxyl group. The alkyl group having 1 to 6 carbon atoms is not specifically limited, but includes, for example, a methyl group, an ethyl group, an n-propyl group, an isopropyl group, a cyclopropyl group, an n-butyl group, a sec-butyl group, a tert-butyl group, an n-pentyl group, a cyclopentyl group, an n-hexyl group, and a cyclohexyl group; and preferably a cyclopropyl group. The substituent is not specifically limited, but includes, for example, an alkyl group such as a methyl group and an ethyl group, a halogen atom, an amino group, and a hydroxyl group.

The aralkyl group having 7 to 15 carbon atoms and optionally having a substituent includes, for example, a benzyl group, a p-chlorobenzyl group, a p-hydroxybenzyl group, a p-fluorobenzyl group, an m,m-difluorobenzyl group, a phenylethyl group, and a naphthyl group. As a preferred combination of $P^1$ and $P^2$, any one of them is a hydrogen and the other is a cyclopropyl group. The substituent is not specifically limited, but includes, for example, a halogen atom, an amino group, and a hydroxyl group, and preferably a halogen atom.

$P^3$ and $P^4$ in the above general formulae (2) and (4) each independently represent a hydrogen atom or a protective group for the amino group, or are joined together to form a phthaloyl group. When any one of $P^3$ and $P^4$ is a protective group for the amino group, the other is preferably a hydrogen atom. In the condensation reaction, it is desirable that both $P^3$ and $P^4$ are not hydrogens at the same time for the purpose of preventing the progress of side reaction.

The protective group for the amino group is a group for protecting an amino group. As the groups to be generally used, the protective groups described in PROTECTIVE GROUPS IN ORGANIC SYNTHESIS 2nd. Ed. (published by JOHN WILEY & SONS in 1991) can be used. The preferred protective groups in the above general formulae (2) and (4) are not specifically limited, but include, for example, carbamate-type protective groups such as a methyloxycarbonyl group, an ethyloxycarbonyl group, a benzyloxycarbonyl group, and a tert-butyloxycarbonyl group; acyl groups such as an acetyl group, a trifluoroacetyl group, a phthaloyl group, and a benzoyl group; aralkyl groups such as a benzyl group, and a dibenzyl group; sulfonyl groups such as a tosyl group, and a mesyl group; and silyl groups such as a trimethylsilyl group. Preferred are carbamate-type protective groups and acyl groups; more preferred are carbamate-type protective groups. Among them, a tert-butyloxycarbonyl group is preferably used. The compound of the above formula (2) may be prepared according to, for example, the process described in WO9807687 and WO0053575.

The absolute configuration of the 2-position and 3-position in the compound of the above formula (2) is not specifically limited, but an optically-active compound having an asymmetric carbon at the 3-position or at both of the 2-position and 3-position is preferable. Especially, a compound having an absolute configuration of (2S,3S) or (2R,3R) at the 2-position and 3-position is preferable as the compound of the above formula (2).

The process for condensation with the above amine (3) is not specifically limited, but may be, for example, dehydrating condensation. The dehydrating condensing agent is not specifically limited, but includes, for example, ethyl-(3-dimethylaminopropyl)-carbodiimide hydrochloride, N,N-dicyclohexylcarbodiimide, and N,N-diisopropylcarbodiimide.

The amount of the condensing agent to be used is not specifically limited, but is, for example, from 0.5 to 10.0 times by mol, preferably from 0.75 to 5.0 times by mol, and more preferably from 1.0 to 2.0 times by mol, relative to the β-(N-protected)amino-α-hydroxycarboxylic acid derivative (2). In the above condensation reaction, if necessary, an activator such as 1-hydroxybenzotriazole, N-hydroxysuccinimide, and N-hydroxy-5-norbornene-2,3-dicarboxyimide may be used. The amount of the activator to be used is not specifically limited, but the lower limit is, for example, preferably 0.01 times by mol, more preferably 0.05 times by mol, and even more preferably 0.1 times by mol, relative to the β-(N-protected)amino-α-hydroxycarboxylic acid derivative (2). The higher limit is preferably 10 times by mol, more preferably 5 times by mol, even more preferably 2 times by mol, and still more preferably 1 time by mol.

The amount of the amine of formula (3) to be used is not specifically limited, but is generally from 0.8 to 10.0 times by mol, more preferably from 0.9 to 5.0 times by mol, and even more preferably from 1.0 to 2.0 times by mol, relative to the β-(N-protected)amino-α-hydroxycarboxylic acid derivative (2).

In the above condensation reaction, if necessary, a base may be added. The base is not specifically limited, but includes amines such as ammonia, triethylamine, and pyridine; and inorganic bases such as potassium carbonate, and sodium hydrogencarbonate.

The reaction solvent includes aliphatic esters such as ethyl acetate, n-propyl acetate, isopropyl acetate, n-butyl acetate, isobutyl acetate, tert-butyl acetate; ethers such as tetrahydrofuran, tert-butyl methyl ether, and ethylene glycol dibutyl ether; nitriles such as acetonitrile; and sulfur-containing solvents such as dimethyl sulfoxide. Among them, preferred are aliphatic esters, and ethers, of which the negative influence as wastes on the environment is relatively small; and more preferred are aliphatic esters. Specifically, as the solvent, ethyl acetate and tetrahydrofuran is preferred; and ethyl acetate is more preferred. Needless-to-say, these solvents may be independently used, and two or more kinds of them may be used in combination. In addition, halogenohydrocarbons such as chloroform, dichloromethane, and 1,2-dichloroethane are also usable as the solvent.

In the reaction with the above-mentioned condensing agent, it is preferable that water coexists in the above-mentioned organic solvent for the purpose of improving the flowability in stirring. The amount of water to be added is not specifically limited, but the lower limit is 0.1 times by weight, preferably 0.3 times by weight, more preferably 0.5 times by weight, and even more preferably 1 time by weight, relative to the above-mentioned condensing agent. The higher limit is not also specifically limited, but is generally 100 times by weight, preferably 30 times by weight, more preferably 10 times by weight, and even more preferably 3 times by weight.

Concerning the reaction temperature, the reaction may be attained at a temperature not lower than that at which the reaction solvent does not solidify, and the temperature is generally not lower than −50° C., preferably not lower than −30° C., even more preferably not lower than 0° C. The higher limit is not specifically limited, but is generally 100° C., preferably 80° C., and more preferably 60° C.

The reaction liquid obtained by the above-mentioned reaction may be washed with water, if necessary. In the washing with water, a base may coexist. The base is not specifically limited, but includes, for example, alkali metal hydroxides such as lithium hydroxide, sodium hydroxide, and potassium hydroxide; alkaline earth metal hydroxides such as calcium hydroxide, and magnesium hydroxide; alkali metal carbonates such as sodium hydrogencarbonate, and potassium hydrogencarbonate; and alkaline earth metal carbonates such as magnesium carbonate, and calcium carbonate. In addition, aqueous ammonia and organic bases such as triethylamine and pyridine are also usable. These may be independently used, and two or more kinds of them may be used.

The operation temperature in the above washing can not be completely determined, as it is dependent on the type of the organic solvent to be used, but the temperature may set from the solidification point to the boiling point of the solvent. The temperature is generally from 0 to 100° C., preferably from 20 to 80° C., and more preferably from 30 to 60° C.

The β-(N-protected)amino-α-hydroxy carboxamide derivative (4) may be directly used in the next step as the extract liquid or concentrated liquid; but if necessary, the derivative may be processed according to an ordinary method, such as crystallization purification, distillation purification, and column chromatography, for further increasing purity thereof.

A method for crystallization of the β-(N-protected)amino-α-hydroxy carboxamide derivative (4) is described herein.

The absolute configuration of the 2-position and 3-position in the compound of the above formula (4) is not specifically limited, but an optically-active compound having an asymmetric carbon at the 3-position or at both of the 2-position and 3-position is preferable. Especially, a compound having an absolute configuration of (2S,3S) or (2R,3R) at the 2-position and 3-position is preferable as the compound of the above formula (4).

The above crystallization is generally attained in the presence of a solvent. The solvent is not specifically limited, but includes, for example, aliphatic esters, and hydrocarbons such as aromatic hydrocarbons and aliphatic hydrocarbons. The aliphatic esters are not specifically limited, but are preferably those having 2 to 8 carbon atoms, and more preferably those having 3 to 6 carbon atoms. Specifically, the aliphatic esters include ethyl acetate, n-propyl acetate, isopropyl acetate, n-butyl acetate, and tert-butyl acetate. Among them, ethyl acetate is preferable. The aromatic hydrocarbons are not specifically limited, but are preferably those having 6 to 12 carbon atoms, more preferably those having 6 to 10 carbon atoms, and even more preferably those having 6 to 8 carbon atoms. Specifically, the aromatic hydrocarbons include, for example, benzene, toluene, and xylene. Among them, toluene is preferable. The aliphatic hydrocarbons are not specifically limited, but are preferably those having 5 to 12 carbon atoms, and more preferably those having 5 to 8 carbon atoms. Specifically, the aliphatic hydrocarbons include, for example, pentane, hexane, heptane, and methylcyclohexane. Among the above-mentioned solvents, aliphatic esters are preferable from the viewpoint of their ability to remove impurities and the production yield. Specifically, ethyl acetate is preferable.

Needless-to-say, the crystallization solvent may be independently used, and two or more kinds of them may be used in combination.

For the crystallization, any ordinary crystallization methods such as cooling crystallization, concentration crystallization, crystallization using solvent substitution, crystallization by mixing poor solvent or salting-out may be employed either independently or suitably in combination.

The crystallization temperature is not specifically limited, but the higher limit is generally 100° C., preferably 80° C., and more preferably 70° C., and the lower limit is a solidification temperature of the crystallization liquid. The lower limit may generally be −30° C., preferably −20° C., and more preferably −10° C.

The crystallization time is not specifically limited, but is generally from 1 to 100 hours, preferably from 1 to 48 hours, and more preferably from 1 to 24 hours.

The crystallization is generally attained with stirring. The agitation power per unit volume is not specifically limited, but is, for example, not less than $0.05$ kW/m$^3$, preferably not less than $0.1$ kW/m$^3$, and more preferably not less than $0.2$ kW/m$^3$.

After the crystallization, the crystal may be separated according to any ordinary solid-liquid separation method such as centrifugation, pressure filtration, and reduced-pressure filtration.

The β-(N-protected)amino-α-hydroxy carboxamide derivative of the above formula (4) containing at least optical isomer thereof as impurity can be crystallized according to the above-mentioned process. Among them, it is preferable to crystallize according to a crystallization process that includes at least one step of the following i) to iii):

i) a step of crystal dissolution
ii) a cooling step
iii) a step of seed crystal addition.

For obtaining the derivative having a higher purity, a combination of i) and ii) or a combination of i) and iii) is preferable, and it is more preferable to carry out all steps i) to iii). In case where the step i) and ii) and/or iii) are combined, the step i) may be carried out first. When both of the steps ii) and iii) are to be carried out, their order is not specifically limited.

The crystallization process gives a crystallization slurry of good flowability, and the crystal obtained by the process is useful due to high purity.

In this case, the solvent to be used in the step i) includes those mentioned in the above for crystallization.

It is preferable that the cooling speed (rate) in the step ii) is not more than 20° C./hr, preferably not more than 10° C./hr, and more preferably not more than 5° C./hr.

The amount of the seed crystal to be added in the step iii) may be suitably determined by experiment and the like; but the amount is generally 1% by weight, preferably 0.1% by weight, and more preferably 0.01% by weight, relative to the β-(N-protected)amino-α-hydroxy carboxamide derivative (4). The crystal seed to be used is not specifically limited, but may be one obtained according to the process of the present invention or may be one obtained separately.

The chemical purity of the β-(N-protected)amino-α-hydroxy carboxamide derivative (4) obtained according to the above-mentioned crystallization process is generally not less than 97%, more preferably not less than 98%, and even more preferably not less than 99%.

The optical purity of the 3-position of the above compound (4) is preferably not less than 98% ee, more preferably not less than 99% ee, and even more preferably not less than 99.5% ee.

Production of the β-amino-α-hydroxy carboxamide derivative (1)

Next, the β-(N-protected)amino-α-hydroxy carboxamide derivative (4) is converted into the β-amino-α-hydroxy carboxamide derivative (1), and then is processed for crystallization to obtain the derivative as a crystal. The steps for obtaining the crystal is described.

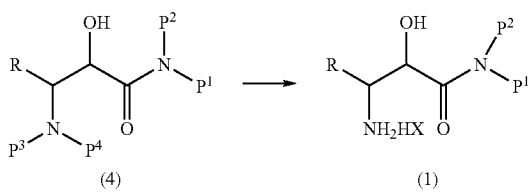

In the above general formula (1), R, $P^1$, $P^2$, $P^3$ and $P^4$ represent the same groups as above. In the step, $P^3$ and $P^4$ may be hydrogens at the same time.

HX includes, for example, a mineral acid, a sulfonic acid and a carboxylic acid. The mineral acid is not specifically limited, but includes hydrogen halides such as hydrogen chloride, and hydrogen bromide; sulfuric acid; phosphoric acid. The sulfonic acid is not specifically limited, but includes, for example, methanesulfonic acid, ethanesulfonic acid, propanesulfonic acid, butanesulfonic acid, benzenesulfonic acid, p-toluenesulfonic acid, camphorsulfonic acid, and 1-phenylethanesulfonic acid. The carboxylic acid is not specifically limited, but includes, for example, non-optically-active carboxylic acids such as formic acid, acetic acid, trifluoroacetic acid, and benzoic acid; optically-active carboxylic acids such as tartaric acid. Among these acids, hydrogen chloride, hydrogen bromide, p-toluenesulfonic acid and benzoic acid that form salts having good crystallinity are preferable; and in particular, hydrogen chloride and hydrogen bromide are preferable, and hydrogen chloride is more preferable.

The β-(N-protected)amino-α-hydroxy carboxamide derivative (4) may be one produced according to the above-mentioned process, or one produced separately according to a known process.

Next, described is a process for converting the β-(N-protected)amino-α-hydroxy carboxamide derivative (4) into the β-amino-α-hydroxy carboxamide derivative (1).

For the reaction of the process, a suitable method may be selected depending on the type of $P^3$ and $P^4$ which represent the N-protective group. For example, when $P^3$ and $P^4$ are a protective group capable of being deprotected with an acid such as tert-butoxycarbonyl, the reaction of the process may be attained by acid treatment.

The absolute configuration of the 2-position and 3-position in the compound of the above formula (4) is not specifically limited, but an optically-active compound having an asymmetric carbon at the 3-position or at both of the 2-position and 3-position is preferable. Especially, the compound of which absolute configuration at the 2-position and 3-position is (2S, 3S) or (2R,3R) is preferable as the compound of the above formula (4).

Hereinafter, the process for reaction with an acid is described.

The acid to be used includes those described in the above as HX.

The amount of the acid to be used may be at least a theoretical amount; but the use thereof in a large amount is not economical. Therefore, the lower limit of the amount is generally not less than 1 time by mol, and the higher limit is generally not more than 10 times by mol, preferably not more than 3 times by mol, and more preferably not more than 2 times by mol, relative to the β-(N-protected)amino-α-hydroxy carboxamide derivative (4).

The acid addition speed (rate) is not specifically limited. For the purpose of preventing rapid generation of carbon dioxide gas that generates with the progress of the reaction, it is desirable that the whole amount of the acid to be used is added, taking at least 1/6 hours, and more preferably at least 1 hour. The higher limit of the addition time is not specifically limited, but the time is preferably at most about 1 day, and preferably at most a half day.

The acid may be added directly as it is, or the aqueous solution or the solution in which the acid is previously dissolved in a solvent mentioned below may be used. When a crystallization step is carried out later, the acid dissolved in the protic solvent mentioned below may be used.

The concentration of the acid to be added is not specifically limited, but the lower limit is generally 0.1% by weight, preferably 1% by weight, more preferably 5% by weight, and even more preferably 10% by weight, and the higher limit is 100% by weight.

The reaction is generally carried out in a solvent. The solvent is not specifically limited, but includes organic solvents such as alcohols, ethers, aliphatic esters, and aromatic hydrocarbons.

The alcohols are not specifically limited, but include, for example, methanol, ethanol, n-propanol, isopropanol, n-butanol, sec-butanol, isobutanol, and tert-butanol. Among them, isopropanol is preferable.

The ethers are not specifically limited, but include, for example, tetrahydrofuran, 1,3-dioxolan, 1,2-dimethoxyethane, diethylene glycol dimethyl ether, and methyl tert-butyl ether. Among them, tetrahydrofuran is preferable. The aliphatic esters are not specifically limited, but are preferably those having 2 to 8 carbon atoms, more preferably those having 3 to 6 carbon atoms. Specifically, the esters include, for example, ethyl acetate, n-propyl acetate, isopropyl acetate, n-butyl acetate, and tert-butyl acetate. Among them, ethyl acetate is preferable. The aromatic hydrocarbons are not specifically limited, but are preferably those having 6 to 12 carbon atoms, more preferably those having 6 to 10 carbon atoms, and even more preferably those having 6 to 8 carbon atoms. Specifically, the aromatic hydrocarbons include, for example, benzene, toluene, and xylene. Among them, preferable are aromatic hydrocarbons having 7 or 8 carbon atoms, and especially toluene and xylene; and toluene is most preferred.

Among the above-mentioned solvents, alcohols are preferable from the viewpoint of the high reactivity and the stability to acid; and isopropanol is more preferred.

In case where $P^3$ and $P^4$ are protective groups that could not be deprotected by acid, the compound is appropriately deprotected according to the type of the protective group, and then is processed with acid according to the above-mentioned process, to obtain the β-amino-α-hydroxy carboxamide derivative (1). In case where $P^3$ and $P^4$ are hydrogens, needless-to-say, deprotection is not required, and the compound may be processed with acid according to the above-mentioned process.

Next, described is a process of crystallization of the β-amino-α-hydroxy carboxamide derivative (1) to thereby collect the derivative as a crystal.

The β-amino-α-hydroxy carboxamide derivative (1) to be processed in the process may be one produced from the β-(N-protected)amino-α-hydroxy carboxamide derivative (4)

according to the above-mentioned process, or one produced separately according to a known method.

The absolute configuration of the 2-position and 3-position in the β-amino-α-hydroxy carboxamide derivative (1) for use in the process is not specifically limited, but an optically-active compound having an asymmetric carbon at the 3-position or at both of the 2-position and 3-position is preferable. Especially, a compound of which absolute configuration of at the 2-position and 3-position is (2S,3S) or (2R,3R) is preferable as the derivative of the above formula (1).

As the impurity contained in the β-amino-α-hydroxy carboxamide derivative (1) for use in the process, the enantiomers thereof can be exemplified.

The crystallization method is not specifically limited, but any ordinary crystallization method such as, for example, reaction crystallization, cooling crystallization, concentration crystallization, crystallization using solvent substitution, crystallization by mixing poor solvent and/or salting-out is employable either independently or suitably in combination. If necessary, a seed crystal may be added in the crystallization.

The crystallization process is carried out in a protic solvent.

The protic solvent is not specifically limited, but includes, for example, alcohols and water. The alcohols are not specifically limited, but include, for example, methanol, ethanol, n-propanol, isopropanol, n-butanol, sec-butanol, isobutanol, and tert-butanol. Among them, isopropanol is preferable. These alcohols may be independently used, and two or more kinds of them may be used in combination.

The protic solvent may be the alcohols alone, or may be a mixed solvent of water and the alcohols. When the mixed solvent is used, the mixing ratio thereof is not specifically limited.

The process in which the β-amino-α-hydroxy carboxamide derivative (1) is produced from the β-(N-protected) amino-α-hydroxy carboxamide derivative (4) according to the above-mentioned process is favorable since the compound (4) can be converted to the compound (1) in one pot from the process of the deprotection step to the acid salt formation step and to the crystallization step, for example, in the protic solvent.

In the crystallization, if necessary, an auxiliary solvent may be used. The auxiliary solvent is used for the purpose of improving, for example, at least one of the yield, the impurity removability and the crystallization liquid flowability.

The auxiliary solvent is not specifically limited, but includes hydrocarbons such as aromatic hydrocarbons, aliphatic hydrocarbons, ethers, and aliphatic esters.

The aromatic hydrocarbons are not specifically limited, but are preferably those having 6 to 12 carbon atoms, more preferably those having 6 to 10 carbon atoms, and even more preferably those having 6 to 8 carbon atoms. Specifically, the aromatic hydrocarbons include, for example, benzene, toluene, and xylene. Among them, toluene is preferable. The aliphatic hydrocarbons are not specifically limited, but are preferably those having 5 to 12 carbon atoms, and more preferably those having 5 to 8 carbon atoms. Specifically, the aliphatic hydrocarbons include, for example, pentane, hexane, heptane, and methylcyclohexane.

The aliphatic ester solvents are not specifically limited, but are preferably those having 2 to 8 carbon atoms, and more preferably those having 3 to 6 carbon atoms. Specifically, the aliphatic ester includes, for example, ethyl acetate, n-propyl acetate, isopropyl acetate, n-butyl acetate, and tert-butyl acetate. Among them, ethyl acetate is preferable. The ether solvents are not specifically limited, but include, for example, tetrahydrofuran, 1,3-dioxolane, 1,2-dimethoxyethane, diethylene glycol dimethyl ether, and methyl tert-butyl ether. Among them, methyl tert-butyl ether is preferable.

Among the above-mentioned auxiliary solvents, the aliphatic hydrocarbons are preferable from the viewpoint of the yield and the improvement of crystallization liquid flowability. Specifically, hexane is preferable. These auxiliary solvents may be independently used, and two or more kinds of them may be used in combination.

When the auxiliary solvent is used, the auxiliary solvent may be previously mixed with the protic solvent, or if necessary, may be suitably added after crystal deposition.

The amount of the protic solvent to be used is not specifically limited, but the lower limit is generally 0.1 times by weight, preferably 0.5 times by weight, more preferably 1 time by weight, and even more preferably 3 times by weight, relative to the β-amino-α-hydroxy carboxamide derivative (1). The higher limit is not specifically limited, but is preferably 100 times by weight, more preferably 30 times by weight, and even more preferably 10 times by weight.

When the cooling crystallization is carried out in the crystallization process, the higher limit of the temperature is not specifically limited so far as it is not higher than the boiling point of the solvent, but the temperature is generally not higher than 100° C., preferably not higher than 80° C., and more preferably not higher than 60° C. The temperature at the end of the cooling is not specifically limited, but is preferably not lower than −20° C., and more preferably not lower than −10° C.

In the cooling crystallization, when the cooling speed (rate) is controlled within a predetermined temperature range, a crystal having a more preferable form can be obtained. Though depending on the solvent, it is important that the cooling speed is kept to be not less than 0.1° C./hr, more preferably not less than 0.5° C./hr, and even more preferably not less than 1° C./hr within a temperature range for crystallization of preferably not higher than 60° C., more preferably not higher than 50° C., and more preferably not higher than 40° C., and preferably not lower than 5° C., more preferably not lower than 10° C., and even more preferably not lower than 15° C. The cooling speed may not be constant so far as kept within the above-mentioned range. When the cooling is carried out at a constant speed, it is also preferable to keep the cooling speed within the above-mentioned range, but the speed is preferably not less than 2° C./hr, more preferably not less than 5° C./hr, and even more preferably not less than 10° C./hr.

The required level of the residual solvent amount in the dry crystal is dependent on the use of the β-amino-α-hydroxy carboxamide derivative (1) and on the stability during storage of the compound and the like; but, in general, the amount is preferably not more than 1%, more preferably not more than 0.5%, and even more preferably not more than 0.2%.

The solvent that is not desired to remain in the crystal includes alcohols such as aliphatic alcohol having 1 to 4 carbon atoms, aromatic alcohol such as phenol; aromatic hydrocarbons such as toluene, and xylene; aliphatic hydrocarbons such as hexane, and heptane; aliphatic esters such as ethyl acetate, and butyl acetate; and ethers such as tetrahydrofuran, 1,4-dioxane, and dimethoxyethane. Among them, aliphatic alcohols having 1 to 4 carbon atoms are undesirable, specifically methanol, ethanol, n-propanol, isopropanol, n-butanol, sec-butanol, tert-butanol are undesirable.

It is preferable for the crystallization to make the crystal to be separated out by strongly stirring at the necessary agitation power per unit volume of not less than 0.05 kW/m$^3$, preferably not less than 0.1 kW/m$^3$, and more preferably not less than 0.3 kW/m$^3$.

Thus obtained crystal of β-amino-α-hydroxy carboxamide derivative (1) can be collected according to an ordinary solid-liquid separation method such as centrifugation, pressure separation and reduced-pressure filtration. If necessary, the obtained crystal may be further processed for reduced-pressure drying, i.e. vacuum drying, to be a dry crystal.

The optical purity of the 3-position of the β-amino-α-hydroxy carboxamide derivative (1) obtained in the manner as above is not less than 98% ee, preferably not less than 99% ee, and more preferably not less than 99.5% ee. The absolute configuration at the 3-position may be (S) form or (R) form.

The diastereomer selectivity of the β-amino-α-hydroxy carboxamide derivative (1) obtained in the manner as above is not less than 95%, preferably not less than 97%, more preferably not less than 99%, and even more preferably not less than 99.5%. The diastereomer selectivity in the present invention is represented as follows: for example, when the absolute configuration of the obtained compound (1) is (2S,3S), the selectivity is represented by a formula {(2S,3S)/(2S,3S)+(2R,3S)}; and when the absolute configuration is (2R,3R), the selectivity is represented by a formula {(2R,3R)/(2R,3R)+(2S,3R)}.

EXAMPLES

The present invention is described in detail with reference to the following Examples. Needless-to-say, these Examples should not whatsoever restrict the invention.

The content amounts of the β-(N-protected)amino-α-hydroxy carboxamide derivative (4) and the β-amino-α-hydroxy carboxamide derivative (1), the amount of the impurity, and the optical purity of the derivative, in the Examples, were determined according to HPLC analysis mentioned below.

Analytical Method for the Content Amounts of [N-cyclopropyl-3-(tert-butoxycarbonyl)amino-2-hydroxyhexanoic acid amide, N-cyclopropyl-3-amino-2-hydroxyhexanoic acid amide hydrochloride], and the impurity Column: Nacalai Cosmosil 5C18-ARII,
Column temperature: 40° C.,
Eluent: phosphoric acid buffer (pH 4.0)/acetonitrile=55/45 (v/v),
Flow rate: 1.0 ml/min,
Detector: UV 210 nm,
Retention time: N-cyclopropyl-3-(tert-butoxycarbonyl)amino-2-hydroxyhexanoic acid amide=5.8 min, N-cyclopropyl-3-amino-2-hydroxyhexanoic acid amide hydrochloride=2.4 min.

Analytical Method for the Content Amount of N-cyclopropyl-3-amino-2-hydroxyhexanoic acid amide hydrochloride and the impurity Column: Nacalai Cosmosil 5C18-ARII,
Column temperature: 40° C.,
Eluent: phosphoric acid buffer (pH 2.5)/acetonitrile=95/5 (v/v),
Flow rate: 1.0 ml/min,
Detector: UV 210 nm,
Retention time: N-cyclopropyl-3-amino-2-hydroxyhexanoic acid amide hydrochloride=6.0 min.

Analytical Method for the Optical Purity of (2S,3S)—N-cyclopropyl-3-(tert-butoxycarbonyl)amino-2-hydroxyhexanoic acid amide Column: Daicel Chiral Pack AD-H,
Column temperature: 30° C.,
Eluent: hexane/isopropanol=95/5 (v/v),
Flow rate: 1.0 ml/min,
Detector: UV 214 nm,
Retention time: (2S,3S)—N-cyclopropyl-3-(tert-butoxycarbonyl)amino-2-hydroxyhexanoic acid amide=10.3 min, (2R,3R)—N-cyclopropyl-3-(tert-butoxycarbonyl)amino-2-hydroxyhexanoic acid amide=13.1 min.

Analytical Method for the Optical Purity of (2S,3S)—N-cyclopropyl-3-amino-2-hydroxyhexanoic acid amide hydrochloride Column: ASTEC CHIROBIOTIC T,
Column temperature: 6° C.,
Eluent: phosphoric acid buffer (pH 3.5)/methanol=20/80 (v/v),
Flow rate: 0.5 ml/min,
Detector: UV 210 nm,
Retention time: (2S,3S)—N-cyclopropyl-3-amino-2-hydroxyhexanoic acid amide hydrochloride=18.6 min, (2R,3R)—N-cyclopropyl-3-amino-2-hydroxyhexanoic acid amide hydrochloride=16.4 min.

Comparative Example 1

(2S,3S)—N-Cyclopropyl-3-(tert-butoxycarbonyl)amino-2-hydroxyhexanoic acid amide

To a DMF (100 mL) solution of (2S,3S)-3-(tert-butoxycarbonyl)amino-2-hydroxyhexanoic acid (41.5 g, 168.0 mmol), 1-Hydroxybenzotriazole (HOBt) monohydrate (27.01 g, 176.4 mmol) and 1-(3-dimethylaminopropyl)-3-ethylcarbodiimide (EDC) hydrochloride (35.43 g, 184.8 mmol) were added. The mixture was cooled by ice. Cyclopropylamine (11.51 g, 201.6 mmol) was dropwise added thereto, and the mixture was stirred for 18 hours with cooling by ice. Next, ethyl acetate (2000 mL) and 5% NaHCO$_3$ aqueous solution (1000 mL) were added thereto in that order, and the aqueous layer was removed. The organic layer was washed twice with 5% NaHCO$_3$ aqueous solution (1000 mL), and further washed with water (1000 mL), to obtain an ethyl acetate solution of (2S,3S)—N-cyclopropyl-3-(tert-butoxycarbonyl)amino-2-hydroxyhexanoic acid amide (yield: 83 mol %).

Comparative Example 2

(2S,3S)—N-Cyclopropyl-3-(tert-butoxycarbonyl)amino-2-hydroxyhexanoic acid amide

Cyclopropylamine (55 mg, 0.97 mmol) was dropwise added to an ethyl acetate (5 mL) solution of (2S,3S)-3-tert-butoxycarbonylamino-2-hydroxyhexanoic acid (200 mg, 0.81 mmol), and the mixture was cooled by ice. HOBt monohydrate (130 mg, 0.85 mmol) and EDC hydrochloride (171 mg, 0.89 mmol) were added thereto, and the mixture was stirred with cooling by ice. As a result, the solid in the mixture aggregated to form a hard lump after about 5 minutes, and the mixture became impossible to be stirred.

Comparative Example 3

(2S,3S)—N-Cyclopropyl-3-amino-2-hydroxyhexanoic acid amide hydrochloride

To a 4 M 1,4-dioxane solution (60 mL) of hydrogen chloride, (2S,3S)—N-cyclopropyl-3-(t-butoxycarbonyl)amino-2-hydroxyhexanoic acid amide (4.5 g) was added. A solid of the product aggregated to form a lump after about 5 minutes, and the flowability of the reaction liquid worsened. After the disappearance of the starting material, the solvent was evaporated away with an evaporator to obtain a concentrated product of (2S,3S)—N-cyclopropyl-3-amino-2-hydroxyhexanoic acid amide hydrochloride (chemical purity: 89.8 area %).

Comparative Example 4

According to the same process as Comparative Example 3, a reaction liquid of (2S,3S)—N-cyclopropyl-3-amino-2-hydroxyhexanoic acid amide hydrochloride was obtained. Then, the precipitated crystals were filtered under reduced pressure, using a Kiriyama funnel (diameter: 4 cm, filter pore size: 4 μm). As a result, the crystals were hardly filterable, and the separation of the crystals from the mother liquid took about 1 hour.

Example 1

(2S,3S)—N-Cyclopropyl-3-(tert-butoxycarbonyl)-amino-2-hydroxyhexanoic acid amide Cyclopropylamine (1.99 g, 34.94 mmol) was dropwise added to a mixed solution of (2S,3S)-3-(tert-butoxycarbonyl)amino-2-hydroxyhexanoic acid (7.2 g, 29.12 mmol), ethyl acetate (144 g) and water (7.2 g). The mixture was cooled by ice. HOBt monohydrate (4.68 g, 30.58 mmol) and EDC hydrochloride (6.14 g, 32.03 mmol) were added thereto, and the mixture was stirred with cooling by ice for 22 hours. Next, 5% NaHCO$_3$ aqueous solution (72 g) was added thereto, and the mixture was heated up to 40° C. Then, the aqueous layer was removed. The organic layer was washed twice with 5% NaHCO$_3$ aqueous solution (72 g) at 40° C., and finally the organic layer was washed with water (72 g), to obtain an ethyl acetate solution of (2S,3S)—N-cyclopropyl-3-(tert-butoxycarbonyl)amino-2-hydroxyhexanoic acid amide (yield: 90 mol %, chemical purity: 96.1 area %, optical purity: 99.3% ee). The obtained organic layer (140.2 g) was concentrated under reduced pressure to be 62.5 g, using a rotary evaporator. The obtained slurry was heated up to 60° C. so as to dissolve the contents, and then cooled to 51° C. Seed crystals of (2S,3S)—N-cyclopropyl-3-(tert-butoxycarbonyl)amino-2-hydroxyhexanoic acid amide (2 mg) were added to the solution. As a result, crystals were gradually precipitated. The mixture was aged at the same temperature for 1 hour, and then was cooled to 2° C., taking about 5 hours. The precipitated crystals were separated and dried to obtain (2S,3S)—N-cyclopropyl-3-(tert-butoxycarbonyl)amino-2-hydroxyhexanoic acid amide (6.45 g, isolation yield: 78 mol %, chemical purity: 100.0 area %, optical purity: 100% ee).

[$^1$H-NMR (CDCl$_3$, 400 MHz/ppm); 0.51 (2H, m), 0.79 (2H, m), 0.92 (3H, t), 1.24-1.70 (13H, m), 2.73 (1H, m), 3.75 (1H, bs), 4.15 (1H, dd), 4.94 (1H, d), 5.17 (1H, d), 6.94 (1H, bs)]

Example 2

(2S,3S)—N-Cyclopropyl-3-(tert-butoxycarbonyl)-amino-2-hydroxyhexanoic acid amide Cyclopropylamine (13.9 g, 242.6 mmol) was dropwise added to a mixed solution of ethyl acetate (250 g)/THF (250 g)=1/1 and (2S,3S)-3-(tert-butoxycarbonyl)amino-2-hydroxyhexanoic acid (50.0 g, 202.2 mmol). The mixture was cooled by ice. A mixed solution of HOBt monohydrate (32.5, 212.3 mmol), EDC hydrochloride (42.6 g, 222.4 mmol) and water (43 g) was dropwise added thereto, and the mixture was stirred for 14 hours with cooling by ice. Next, 5% NaHCO$_3$ aqueous solution (250 g) was added thereto, and the mixture was heated up to 40° C. Then, the aqueous layer was removed, and the organic-layer was washed twice with 5% NaHCO$_3$ aqueous solution (250 g) at 40° C. and finally washed with water (250 g), to obtain a solution of (2S,3S)—N-cyclopropyl-3-(tert-butoxycarbonyl)-amino-2-hydroxyhexanoic acid amide (reaction yield: 95 mol %, extraction yield: 89 mol %, chemical purity: 96.9 area %).

Example 3

(2S,3S)—N-Cyclopropyl-3-(tert-butoxycarbonyl)-amino-2-hydroxyhexanoic acid amide Cyclopropylamine (2.77 g, 48.53 mmol) was dropwise added to an ethyl acetate (108 g) solution of (2S,3S)-3-(tert-butoxycarbonyl)amino-2-hydroxyhexanoic acid (10.0 g, 40.44 mmol). The mixture was cooled by ice. A mixed solution of HOBt monohydrate (1.86 g, 12.13 mmol)/THF (9.3 g)/water (1.9 g)=1/5/1 and a mixed solution of EDC hydrochloride (8.53 g, 44.48 mmol)/water (8.5 g)=1/1 were dropwise added in that order, and the mixture was stirred for 14 hours with cooling by ice. Next, 5% NaHCO$_3$ aqueous solution (50 g) was added, and the mixture was heated up to 40° C. Then, the aqueous layer was removed. The organic layer was washed once with 5% NaHCO$_3$ aqueous solution (50 g) at 40° C., and finally washed with water (50 g), to obtain a solution of (2S,3S)—N-cyclopropyl-3-(tert-butoxycarbonyl)amino-2-hydroxyhexanoic acid amide (reaction yield: 97 mol %, extraction yield: 98 mol %, chemical purity: 96.0 area %).

Example 4

(2S,3S)—N-Cyclopropyl-3-amino-2-hydroxyhexanoic acid amide hydrochloride

Isopropanol (250 mL) was added to (2S,3S)—N-cyclopropyl-3-(tert-butoxycarbonyl)amino-2-hydroxyhexanoic acid amide (26.5 g, 92.54 mmol), and the mixture was heated up to about 60° C. To the solution, 35% hydrochloric acid aqueous solution (14.5 g, 138.8 mmol) was dropwise added, and the mixture was stirred for 24 hours. After the disappearance of the starting material, the reaction liquid for the remove of Boc function group was cooled from 60° C. to 2° C. at a constant cooling rate, taking about 6 hours. As a result, no solid aggregated and the flowability thereof was good. The precipitated crystals were collected by filtration under reduced pressure, using a Kiriyama funnel (diameter 6 cm, filter pore size 4 μm). At the time, the filterability was good and the time for the separation of the crystals from the mother liquid was about 60 seconds. By the isolation and drying in vacuum, (2S,3S)—N-cyclopropyl-3-amino-2-hydroxyhexanoic acid amide hydrochloride (16.53 g) was obtained as white crystals (yield: 80 mol %, isopropanol content: no isopropanol detected, chemical purity: 100.0 area %, optical purity: 100% ee).

[$^1$H-NMR (CD$_3$)$_2$SO, 400 MHz/ppm); 0.52 (2H, m), 0.63 (2H, m), 0.86 (3H, t), 1.25-1.50 (4H, m), 2.69 (1H, m), 3.39 (1H, bs), 4.22 (1H, bs), 6.27 (1H, bs), 8.04 (4H, bs)]

Example 5

(2S,3S)—N-Cyclopropyl-3-amino-2-hydroxyhexanoic acid amide hydrochloride

The ethyl acetate solution of (2S,3S)—N-cyclopropyl-3-(tert-butoxycarbonyl)amino-2-hydroxyhexanoic acid amide obtained in the above Example 2 was concentrated to dryness. Isopropyl alcohol (29.9 g) was added to the concentrated product (97.4 wt %, 96.9 area %, 5.13 g), and the mixture was heated up to 60° C. for dissolution. Next, 10.5 wt % hydrogen chloride/isopropyl alcohol solution (9.1 g) was dropwise added, taking 1 hour. After stirred for 8 hours, the reaction solution was cooled down to 0° C. at a constant rate, taking about 6 hours. The slurry had no solid aggregation therein, and had good flowability. The precipitated crystals were collected by filtration under reduced pressure, using a kiriyama funnel (diameter 4 cm, filter pore size 4 μm). At the time, filterability was good, and the time taken for separation of the crystals from the mother liquid was about 30 seconds. The obtained wet crystals were washed with hexane/isopropyl alcohol=1/1 solution (15 mL). Next, the washed wet crystals were dried in vacuum at 60° C., to obtain (2S,3S)—N-cyclopropyl-3-amino-2-hydroxyhexanoic acid amide hydrochloride (3.33 g, isolation yield: 89 mol %, chemical purity: 100.0 area %, optical purity: 100% ee).

Example 6

(2S,3S)—N-Cyclopropyl-3-amino-2-hydroxyhexanoic acid amide hydrochloride

The ethyl acetate solution of (2S,3S)—N-cyclopropyl-3-(tert-butoxycarbonyl)amino-2-hydroxyhexanoic acid amide (92.2 g, 10.8 wt. %) obtained in the above Example 2 was used. The solvent was changed from ethyl acetate to isopropyl alcohol, thereby to prepare an isopropyl alcohol solution of (2S,3S)—N-cyclopropyl-3-(tert-butoxycarbonyl)amino-2-hydroxyhexanoic acid amide (69.63 g). The solution was heated up to 60° C., and 10.5 wt % hydrogen chloride/isopropyl alcohol solution (18.2 g) was dropwise added, taking 1 hour. After stirred for 8 hours, the reaction solution was cooled down to 0° C. at a constant rate, taking about 6 hours. The slurry had no solid aggregation therein, and had good flowability. The precipitated crystals were collected by filtration under reduced pressure, using a kiriyama funnel (diameter 6 cm, filter pore size 4 μm). At the time, the filterability was good, and the time taken for separation of the crystals from the mother liquid was about 30 seconds. The obtained wet crystals were washed with hexane/isopropyl alcohol=1/1 solution (30 mL). Next, the washed wet crystals were dried in vacuum at 60° C., to obtain (2S,3S)—N-cyclopropyl-3-amino-2-hydroxyhexanoic acid amide hydrochloride (7.06 g, isolation yield: 90 mol %, chemical purity: 100.0 area %, optical purity: 100% ee).

Example 7

(2S,3S)—N-Cyclopropyl-3-amino-2-hydroxyhexanoic acid amide hydrochloride

The ethyl acetate solution of (2S,3S)—N-cyclopropyl-3-(tert-butoxycarbonyl)amino-2-hydroxyhexanoic acid amide (46.1 g, 10.8 wt. %) obtained in the above Example 2 was used. The solvent was changed from ethyl acetate to isopropyl alcohol, thereby to prepare an isopropyl alcohol solution of (2S,3S)—N-cyclopropyl-3-(tert-butoxycarbonyl)amino-2-hydroxyhexanoic acid amide (34.82 g). Hexane (20 g) was added to the solution and the mixture was heated up to 60° C., and 10.5 wt % hydrogen chloride/isopropyl alcohol solution (9.1 g) was dropwise added, taking 1 hour. Then, after stirred for 8 hours, the reaction solution was cooled down to 0° C. at a constant rate, taking about 6 hours. The slurry had no solid aggregation therein, and had good flowability. The precipitated crystals were collected by filtration under reduced pressure, using a kiriyama funnel (diameter 4 cm, filter pore size 4 μm). At the time, the filterability was good, and the time taken for separation of the crystals from the mother liquid was about 30 seconds. The obtained wet crystals were washed with hexane/isopropyl alcohol=1/1 solution (15 mL). Next, the washed wet crystals were dried in vacuum at 60° C., to obtain (2S,3S)—N-cyclopropyl-3-amino-2-hydroxyhexanoic acid amide hydrochloride (3.48 g, yield: 90 mol %, chemical purity: 100.0 area %, optical purity: 100% ee).

Example 8

(2S,3S)—N-Cyclopropyl-3-amino-2-hydroxyhexanoic acid amide hydrochloride

The reaction liquid for the remove of Boc function group (about 273 g) obtained in Example 4 was cooled from 60° C. to 20° C., taking 12 hours. The liquid was cooled from 20° C. to 15° C., taking 7 hours, and then further to 2° C., taking 3 hours. During the cooling, the liquid had no solid aggregation therein, and the flowability was good. The precipitated crystals were collected by filtration under reduced pressure, using a kiriyama funnel (diameter 6 cm, filter pore size 4 μm), then was dried in vacuum at a drying temperature of 60° C. for 4 days, to obtain (2S,3S)—N-cyclopropyl-3-amino-2-hydroxyhexanoic acid amide hydrochloride as white crystals (16.53 g, yield: 80 mol %, isopropanol content: 0.15%, chemical purity: 100.0 area %, optical purity: 100% ee).

Example 9

(2S,3S)—N-Cyclopropyl-3-amino-2-hydroxyhexanoic acid amide hydrochloride

The reaction liquid for the remove of Boc function group (about 273 g) obtained in Example 4 was cooled from 60° C. to 2° C. at a constant rate, taking 20 hours. During the cooling, the liquid had no solid aggregation therein, and the flowability was good. The precipitated crystals were collected by filtration under reduced pressure, using a kiriyama funnel (diameter 6 cm, filter pore size 4 μm). Then, the crystals were dried in vacuum at a drying temperature of 60° C. for 4 days, to obtain (2S,3S)—N-cyclopropyl-3-amino-2-hydroxyhexanoic acid amide hydrochloride as white crystals (16.71 g, yield: 81 mol %, isopropanol content: 0.03%, chemical purity: 100.0 area %, optical purity: 100% ee).

The invention claimed is:
1. A process for production of a β-amino-α-hydroxy carboxamide derivative (1) of the following general formula (1);

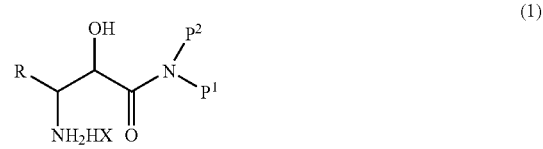

(wherein R represents an alkyl group having 1 to 6 carbon atoms and optionally having a substituent, or an aralkyl group having 7 to 15 carbon atoms and optionally having a substituent;
$P^1$ and $P^2$ each independently represent a hydrogen atom, an alkyl group having 1 to 6 carbon atoms and optionally having a substituent, an aralkyl group having 7 to 15 carbon atoms and optionally having a substituent, or a carboxyl group; HX represents a mineral acid, a sulfonic acid, or a carboxylic acid)
characterized in that the β-amino-α-hydroxy carboxamide derivative (1) is obtained as a crystal by a crystallization step using a solvent containing a protic solvent.

2. The process for production according to claim 1, comprising a step of deprotecting a β-(N-protected)amino-α-hydroxy carboxamide derivative of the following general formula (4);

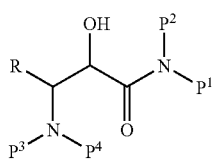
(4)

(wherein R, P¹ and P² are the same group as above; P³ and P⁴ each independently represent a hydrogen atom or a protective group for the amino group, or are joined together to form a phthaloyl group) for conversion to the β-amino-α-hydroxy carboxamide derivative (1).

3. The process for production according to claim 2, wherein the deprotection is attained with an acid.

4. The process for production according to claim 3, wherein an amount of the acid to be used is not less than 1 time by mol relative to the β-(N-protected)amino-α-hydroxy carboxamide derivative (4).

5. The process for production according to claim 1, wherein the protic solvent is an alcohol or a mixed solvent of an alcohol and water.

6. The process for production according to claim 1, wherein cooling crystallization at a cooling speed of not less than 1° C./hr is carried out in the crystallization step.

7. The process for production according to claim 1, wherein the compound of the formula (1) is obtained by deprotecting a β-(N-protected)amino-α-hydroxy carboxamide derivative of the following general formula (4);

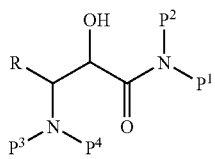
(4)

(wherein R, P¹ and P² are the same group as above; P³ and P⁴ each independently represent a hydrogen atom or a protective group for the amino group, or are joined together to form a phthaloyl group),
and the β-(N-protected)amino-α-hydroxy carboxamide derivative (4) is produced by the reaction of a β-amino-α-hydroxycarboxylic acid of the following general formula (2);

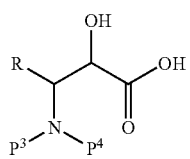
(2)

(wherein R, P³ and P⁴ are the same as above) with a condensing agent and an amine of the general formula (3);

$P^1P^2NH$ (3)

(wherein $P^1$ and $P^2$ are the same as above) in the presence of one or more solvents of aliphatic esters, ethers, nitriles and sulfur-containing solvents.

8. The process for production according to claim 2, wherein an absolute configuration of the 2-position and 3-position in the compound of the formula (4) is (2S,3S) or (2R,3R).

9. The process for production according to claim 1, wherein R is an n-propyl group.

10. The process for production according to claim 1, wherein one of P¹ and P² is a hydrogen atom and the other is a cyclopropyl group.

11. The process for production according to claim 2, wherein one of P³ and P⁴ is a hydrogen atom and the other is a tert-butoxycarbonyl group.

12. The process for production according to claim 1, wherein HX is hydrogen chloride.

* * * * *